(12) United States Patent
Kommuri et al.

(10) Patent No.: US 10,787,402 B2
(45) Date of Patent: Sep. 29, 2020

(54) SEPARATION OF OFF GASES FROM C3 HYDROCARBONS IN PROPANE DEHYDROGENATION PROCESS

(71) Applicant: SABIC Global Technologies B.V., Bergen op Zoom (NL)

(72) Inventors: Subba Rao Kommuri, Riyadh (SA); Mohamed Sabri Abdelghani, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/075,004

(22) PCT Filed: Apr. 13, 2017

(86) PCT No.: PCT/IB2017/052146
§ 371 (c)(1),
(2) Date: Aug. 2, 2018

(87) PCT Pub. No.: WO2017/179009
PCT Pub. Date: Oct. 19, 2017

(65) Prior Publication Data
US 2019/0047923 A1 Feb. 14, 2019

Related U.S. Application Data

(60) Provisional application No. 62/322,981, filed on Apr. 15, 2016.

(51) Int. Cl.
*C07C 7/11* (2006.01)
*B01D 53/14* (2006.01)
(Continued)

(52) U.S. Cl.
CPC .............. *C07C 7/11* (2013.01); *B01D 3/00* (2013.01); *B01D 3/14* (2013.01); *B01D 53/1418* (2013.01);
(Continued)

(58) Field of Classification Search
CPC .. C07C 7/00; C07C 7/005; C07C 7/04; C07C 7/11
(Continued)

(56) References Cited

U.S. PATENT DOCUMENTS 2,516,507 A 7/1950 Deming .................... 183/115
2,573,341 A 10/1951 Kniel ......................... 260/683
(Continued)

FOREIGN PATENT DOCUMENTS

CN 1689688 A 11/2005
CN 101087740 A 12/2007
(Continued)

OTHER PUBLICATIONS

International Search Report and Written Opinion from PCT/IB2017/052146 dated Jun. 28, 2017, 11 pages.

*Primary Examiner* — Thuan D Dang
(74) *Attorney, Agent, or Firm* — Norton Rose Fulbright US LLP

(57) ABSTRACT

Methods and systems for separating $C_3$ hydrocarbons from lighter hydrocarbons, carbon monoxide, carbon dioxide, and water are provided. In certain embodiments, the methods include feeding a gaseous mixture including $C_1$, $C_2$, and $C_3$ hydrocarbons and benzene solvent to the absorber column where benzene solvent selectively absorbs $C_3$ hydrocarbons. The methods can further include removing a first stream comprising benzene solvent and absorbed $C_3$ hydrocarbons from the absorber column, and feeding the first stream to a stripper column where benzene solvent is separated from $C_3$ hydrocarbons, and removing a second stream comprising $C_3$ hydrocarbons from the stripper column.

20 Claims, 2 Drawing Sheets

(51) Int. Cl.

| | | |
|---|---|---|
| | *C10G 70/06* | (2006.01) |
| | *C10G 7/00* | (2006.01) |
| | *B01D 3/00* | (2006.01) |
| | *C10G 5/04* | (2006.01) |
| | *B01D 3/14* | (2006.01) |
| | *C07C 7/04* | (2006.01) |
| | *C07C 7/00* | (2006.01) |
| | *C07C 9/04* | (2006.01) |
| | *C07C 9/06* | (2006.01) |
| | *C07C 9/08* | (2006.01) |
| | *C07C 11/04* | (2006.01) |
| | *C07C 11/06* | (2006.01) |

(52) U.S. Cl.
CPC ..... *B01D 53/1425* (2013.01); *B01D 53/1487* (2013.01); *B01D 53/1493* (2013.01); *C07C 7/04* (2013.01); *C10G 5/04* (2013.01); *C10G 7/00* (2013.01); *C10G 70/06* (2013.01); *B01D 53/1406* (2013.01); *B01D 2252/205* (2013.01); *B01D 2257/7022* (2013.01); *C07C 7/005* (2013.01); *C07C 9/04* (2013.01); *C07C 9/06* (2013.01); *C07C 9/08* (2013.01); *C07C 11/04* (2013.01); *C07C 11/06* (2013.01); *C10G 2300/4081* (2013.01); *Y02P 20/51* (2015.11)

(58) Field of Classification Search
USPC ........................................ 585/809, 833, 867
See application file for complete search history.

(56) References Cited

U.S. PATENT DOCUMENTS

| | | | |
|---|---|---|---|
| 4,479,812 | A | 10/1984 | Hsia et al. ............... 55/48 |
| 4,832,718 | A | 5/1989 | Mehra ..................... 62/17 |
| 5,019,143 | A | 5/1991 | Mehrta ..................... 62/17 |
| 2008/0221374 | A1 | 9/2008 | Crone et al. |
| 2008/0269536 | A1 | 10/2008 | Crone et al. |
| 2009/0240094 | A1 | 9/2009 | Crone et al. |

FOREIGN PATENT DOCUMENTS

| | | |
|---|---|---|
| CN | 101115697 A | 1/2008 |
| CN | 103420757 A | 12/2013 |
| GB | 608091 A | 9/1948 |
| WO | WO2015063214 A1 | 5/2015 |

SEPARATION OF OFF GASES FROM C3 HYDROCARBONS IN PROPANE DEHYDROGENATION PROCESS

CROSS-REFERENCE TO RELATED APPLICATIONS

This application is a national phase application under 35 U.S.C. §371 of International Application No. PCT/IB2017/052146 filed Apr. 13, 2017, which claims priority to United States Provisional Patent Application No. 62/322,981 filed Apr. 15, 2016. The entire contents of each of the above-referenced disclosures is specifically incorporated by reference herein without disclaimer.

FIELD

The presently disclosed subject matter relates to methods and systems for separating $C_3$ hydrocarbons from lighter hydrocarbons by using benzene as a solvent in absorber-stripper columns.

BACKGROUND

Propene can be produced from fossil fuels, e.g., petroleum, natural gas, and coal. Propene is a byproduct of oil refining and natural gas processing. As cracker feeds have become lighter, favoring ethylene production, propylene shortages have brought on the need for "on-purpose" propylene productions from the dehydrogenation of propane to propylene. In these "on purpose" propylene productions, reactor effluent can contain many other components apart from the desired reaction product, mainly due to side reactions and unconverted feed.

Undesirable components need to be separated from the reactor effluent stream in order to obtain more pure product. Propane dehydrogenation reactor effluent mainly contains unreacted propane feed and other off gases including hydrogen ($H_2$), carbon monoxide (CO), carbon dioxide ($CO_2$), methane, ethane, ethylene, water, and/or other heavier components apart from the desired product, propylene.

In olefin dehydrogenation processes, certain conventional distillation techniques are used to separate certain "off gases" from the main reaction product, and is dependent on the boiling point temperatures of such off gases. With boiling point temperatures well below 0° C., cold box and compressors apart from distillation columns are required to achieve the desired separation, which result in high capital and operational costs.

There remains a need for improved systems and methods for separating off gases from $C_3$ hydrocarbons in propane dehydrogenation process.

SUMMARY

The presently disclosed subject matter provides methods and systems for separating $C_3$ hydrocarbons from a gaseous mixture including $C_1$, $C_2$, and $C_3$ hydrocarbons. One non-limiting example includes feeding a gaseous mixture including $C_1$, $C_2$, and $C_3$ hydrocarbons to an absorber column, and feeding benzene solvent to the absorber column where benzene solvent selectively absorbs $C_3$ hydrocarbons. This method can also include removing a first stream including benzene solvent and absorbed $C_3$ hydrocarbons from the absorber column, and feeding the first stream to a stripper column where benzene solvent is separated from $C_3$ hydrocarbons. This method can further include removing a second stream including $C_3$ hydrocarbons from the stripper column.

In certain embodiments, the gaseous mixture further includes hydrogen, carbon monoxide, carbon dioxide, water, or combinations thereof. The first stream can be removed from the bottom of the absorber column. The second stream can be removed from the top of the stripper column. In certain embodiments, the $C_1$ hydrocarbons include methane. In certain embodiments, the $C_2$ hydrocarbons include ethane, ethylene, or combinations thereof. In certain embodiments, the $C_3$ hydrocarbons include propane, propylene, or combinations thereof.

The method can further include removing a third stream comprising $C_1$ and $C_2$ hydrocarbons from the absorber column. The third stream can be removed from the top of the absorber column. The method can further include removing a fourth stream including benzene solvent from the stripper column. The fourth stream can be removed from the bottom of the stripper column. In certain embodiments, the method can further include feeding the fourth stream to the absorber column. The method can further include purging the fourth stream prior to feeding to the absorber column. In addition, the method can further include feeding the second stream to a $C_3$ stripper column to separate propane from propylene.

In certain embodiments, the benzene solvent is in countercurrent contact with the gaseous mixture. In certain embodiments, the weight ratio of the benzene solvent fed to the absorber column to the gaseous mixture fed to the absorber column is from about 3:1 to about 4:1 (ton/ton). In certain embodiments, the weight ratio of the benzene solvent fed to the absorber column to the gaseous mixture fed to the absorber column is about 4:1 (ton/ton). In certain embodiments, the weight ratio of the benzene solvent fed to the absorber column to the gaseous mixture fed to the absorber column is about 3.6:1 (ton/ton).

In accordance with the presently disclosed subject matter, the pressure of the absorber column can be maintained at a pressure of from about 23 bar to about 24 bar. The pressure of the stripper column can be maintained at a pressure of from about 22 bar to about 23 bar. The temperature of the top of the absorber column can be maintained at a temperature of from about 7° C. to about 8° C. The temperature of the bottom of the absorber column can be maintained at a temperature of from about 100° C. to about 150° C. The temperature of the top of the stripper column can be maintained at a temperature of from about 50° C. to about 60° C. The temperature of the bottom of the stripper column can be maintained at a temperature of from about 220° C. to about 230° C.

The presently disclosed subject matter further provides systems for separating $C_3$ hydrocarbons from a gaseous mixture comprising $C_1$, $C_2$, and $C_3$ hydrocarbons using a benzene solvent. One non-limiting example includes an absorber column configured to receive the benzene solvent and the gaseous mixture, to promote the selective absorption of $C_3$ hydrocarbons from the gaseous mixture by the benzene solvent. The system can further include a stripper column configured to receive a first stream including the benzene solvent and absorbed $C_3$ hydrocarbons withdrawn from the absorber column, such that the benzene solvent is separated from $C_3$ hydrocarbons in the stripper column. The system can further include a $C_3$ stripper column configured to receive a second stream including $C_3$ hydrocarbons withdrawn from the stripper column, such that propane is separated from propylene.

Also disclosed in the context of the present invention are embodiments 1-20. Embodiment 1 is a method for separating $C_3$ hydrocarbons from a gaseous mixture comprising $C_1$, $C_2$, and $C_3$ hydrocarbons, the method comprising: (a) feeding the gaseous mixture to an absorber column; (b) feeding benzene solvent to the absorber column, wherein benzene solvent selectively absorbs $C_3$ hydrocarbons; (c) removing a first stream comprising benzene solvent and absorbed $C_3$ hydrocarbons from the absorber column; (d) feeding the first stream to a stripper column where benzene solvent is separated from $C_3$ hydrocarbons; and (e) removing a second stream comprising $C_3$ hydrocarbons from the stripper column. Embodiment 2 is the method of embodiment 1, wherein the gaseous mixture further comprises hydrogen, carbon monoxide, carbon dioxide, water or combinations thereof. Embodiment 3 is the method of any one of embodiments 1 or 2, wherein the $C_1$ hydrocarbons comprise methane. Embodiment 4 is the method of any one of embodiments 1 to 3, wherein the $C_2$ hydrocarbons comprise ethane, ethylene, or combinations thereof. Embodiment 5 is the method of any one of embodiments 1 to 4, wherein the $C_3$ hydrocarbons comprise propane, propylene, or combinations thereof. Embodiment 6 is the method of any one of embodiments 1 to 5, further comprising removing a third stream comprising $C_1$ and $C_2$ hydrocarbons from the absorber column. Embodiment 7 is the method of embodiment 6, further comprising removing a fourth stream comprising benzene solvent from the stripper column. Embodiment 8 is the method of embodiment 7, further comprising feeding the fourth stream to the absorber column. Embodiment 9 is the method of any one of embodiments 1 to 8, further comprising feeding the second stream to a $C_3$ stripper column to separate propane from propylene. Embodiment 10 is the method of any one of embodiments 1 to 9, wherein the benzene solvent is in countercurrent contact with the gaseous mixture. Embodiment 11 is the method of any one of embodiments 1 to 10, wherein the weight ratio of the benzene solvent fed to the absorber column to the gaseous mixture fed to the absorber column is from about 3:1 to about 4:1 (ton/ton). Embodiment 12 is the method of any one of embodiments 1 to 11, wherein the pressure of the absorber column is maintained at a pressure of from about 23 bar to about 24 bar. Embodiment 13 is the method of any one of embodiments 1 to 12, wherein the pressure of the stripper column is maintained at a pressure of from about 22 bar to about 23 bar. Embodiment 14 is the method of any one of embodiments 1 to 13, wherein the temperature of the top of the absorber column is maintained at a temperature of from about 7° C. to about 8° C. Embodiment 15 is the method of any one of embodiments 1 to 14, wherein the temperature of the bottom of the absorber column is maintained at a temperature of from about 100° C. to about 150° C. Embodiment 16 is the method of any one of embodiments 1 to 15, wherein the temperature of the top of the stripper column is maintained at a temperature of from about 50° C. to about 60° C. Embodiment 17 is the method of any one of embodiments 1 to 16, wherein the temperature of the bottom of the stripper column is maintained at a temperature of from about 220° C. to about 230° C.

Embodiment 18 is a system for separating $C_3$ hydrocarbons from a gaseous mixture comprising $C_1$, $C_2$, and $C_3$ hydrocarbons using a benzene solvent, the system comprising: (a) an absorber column configured to receive the benzene solvent and the gaseous mixture, and to promote the selective absorption of $C_3$ hydrocarbons from the gaseous mixture by the benzene solvent; and (b) a stripper column configured to receive a first stream comprising the benzene solvent and absorbed $C_3$ hydrocarbons withdrawn from the absorber column, such that the benzene solvent is separated from $C_3$ hydrocarbons in the stripper column. Embodiment 19 is the system of embodiment 18, further comprising a $C_3$ stripper column configured to receive a second stream comprising $C_3$ hydrocarbons withdrawn from the stripper column, such that propane is separated from propylene. Embodiment 20 is the system of any one of embodiments 18 to 19, wherein the weight ratio of the benzene solvent fed to the absorber column to the gaseous mixture fed to the absorber column is from about 3:1 to about 4:1 (ton/ton).

DETAILED DESCRIPTION

The presently disclosed subject matter provides processes and systems for separating $C_3$ hydrocarbons from a gaseous mixture.

Figure 1:
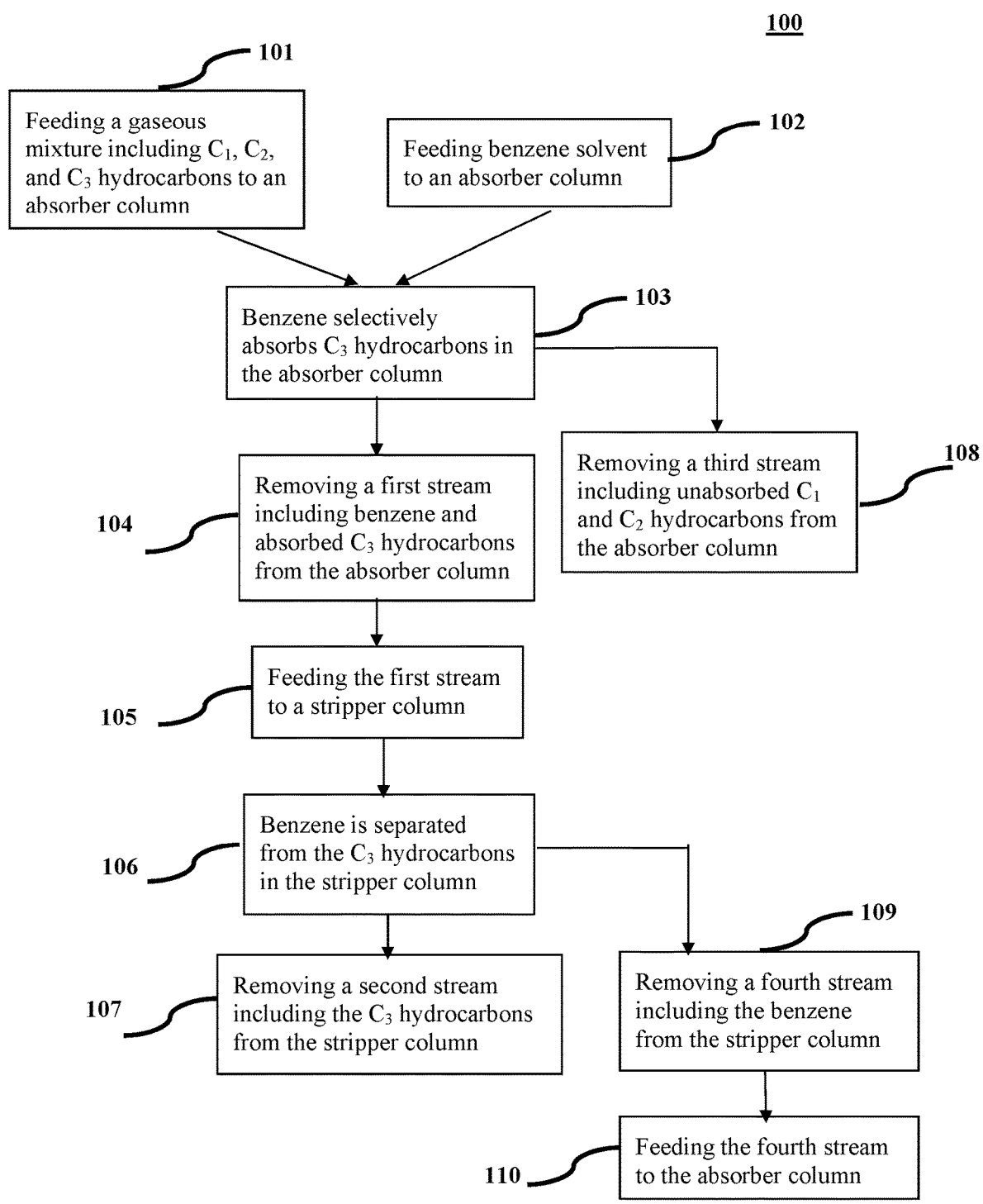
FIG. 1 is a schematic diagram depicting an exemplary method in accordance with one non-limiting embodiment of the disclosed subject matter.

For the purpose of illustration and not limitation, FIG. 1 a schematic representation of an exemplary method according to the disclosed subject matter. In certain embodiments, the method 100 includes feeding a gaseous mixture including $C_1$, $C_2$, and $C_3$ hydrocarbons to an absorber column 101.

In certain embodiments, the gaseous mixture is a reactor effluent from a process for producing propylene. The process for producing propylene can be an "on-purpose" propylene production process. "On-purpose" propylene production processes include, but are not limited to, metathesis, propane dehydrogenation, methanol-to-olefins/methanol-to-propylene, high severity fluid-catalytic cracking (FCC) process, and olefins cracking. In certain embodiments, the process for producing propylene is a propane dehydrogenation process. In certain embodiments, dehydrogenation of propane includes the breaking of two carbon-hydrogen bonds with the simultaneous formation of a hydrogen molecule as shown below. The reaction is endothermic and requires high temperatures.

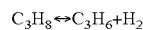

In certain embodiments, a propane dehydrogenation process includes dehydrogenating propane in the presence of oxygen, as shown below. This process is exothermal, and has no equilibrium limitation.

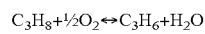

In certain embodiments, a propane dehydrogenation process includes dehydrogenating propane in the presence of steam as shown below.

In certain embodiments, a propane dehydrogenation process includes dehydrogenating propane in the presence of steam and oxygen. In certain embodiments, a reactor effluent can include propylene, unreacted feed propane, and off gases. The off gases can include at least one of hydrogen ($H_2$), carbon monoxide (CO), carbon dioxide ($CO_2$), $C_1$ hydrocarbons, $C_2$ hydrocarbons, and water.

In certain embodiments, the $C_1$ hydrocarbons include methane. In certain embodiments, the $C_2$ hydrocarbons include ethane, ethylene, acetylene, or combinations thereof. In certain embodiments, the $C_3$ hydrocarbons include propylene, propane, methylacetylene, and combinations thereof.

The composition of the gaseous mixture can vary depending on the operation condition, the presence of steam or oxygen, and/or the quantity of steam and/or oxygen. The process conditions, e.g., solvent flow rate, solvent temperature, and absorber pressure, can be modified to have $C_3$ hydrocarbons selectively absorbed by the benzene solvent depending on the composition of the gaseous mixture (e.g., the reactor effluent composition).

In certain embodiments, the gaseous mixture is compressed in a multi-stage compressor to increase the pressure and to remove water prior to entering the Absorber column. Following the compressor, the gaseous mixture can further go through one or more dryer to remove remaining moisture.

In certain embodiments, the method 100 includes feeding a benzene solvent to the absorber column 102. In the absorber column, benzene selectively absorbs $C_3$ hydrocarbons 103, e.g., benzene does not absorb $C_1$ hydrocarbons, $C_2$ hydrocarbons, $H_2$, CO, or $CO_2$. The benzene solvent can be in the countercurrent or concurrent contact with the gaseous mixture. In certain embodiments, the benzene solvent is in the countercurrent contact with the gaseous mixture.

The amount of the benzene solvent fed to the absorber column can be determined and/or adjusted depending on the amount of gaseous mixture fed to the absorber column. The weight ratio of the benzene solvent fed to the absorber column to the gaseous mixture fed to the absorber column can be from about 1:1 to about 5:1 (ton/ton). In certain embodiments, the weight ratio of the benzene solvent fed to the absorber column to the gaseous mixture fed to the absorber column is from about 3:1 to about 4:1 (ton/ton), e.g., about 3:1, about 3.1:1, about 3.2:1, about 3.3:1, about 3.4:1, about 3.5:1, about 3.6:1, about 3.7:1, about 3.8:1, about 3.9:1, or about 4:1. In certain embodiments, the weight ratio of the benzene solvent fed to the absorber column to the gaseous mixture fed to the absorber column is about 4:1 (ton/ton). In certain embodiments, the weight ratio of the benzene solvent fed to the absorber column to the gaseous mixture fed to the absorber column is about 3.6:1 (ton/ton).

As used herein, the term "about" or "substantially" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

The method 100 includes removing a first stream including the benzene solvent and the $C_3$ hydrocarbons absorbed by benzene from the absorber column 104. In certain embodiments, the first stream is removed from the bottom stream of the absorber column. The method 100 can further include removing a third stream including the unabsorbed $C_1$ hydrocarbons, $C_2$ hydrocarbons, $H_2$, CO, and $CO_2$ from the absorber column 108. In certain embodiments, the third stream is removed from the top of the absorber column. Thus, the $C_3$ hydrocarbons are separated from other components of the gaseous mixture, e.g., $C_1$ hydrocarbons, $C_2$ hydrocarbons, $H_2$, CO, and $CO_2$, in the absorber column. Because the third stream can be rich in $H_2$, the third stream can be used as fuel for a propane dehydrogenation reaction. The method can further include purifying $H_2$ from the third stream and the purified $H_2$ can be used as fuel for a propane dehydrogenation reaction.

The pressure of the top and the bottom of the absorber column can be different, substantially the same, or the same. The pressure of the top of the absorber column can be maintained from about 10 bar to about 40 bar. In certain embodiments, the pressure of the top of the absorber column is from about 20 bar to about 30 bar, e.g., from about 20 bar to about 25 bar (e.g., from about 20 bar to about 21 bar, from about 21 bar to about 22 bar, from about 22 bar to about 23 bar, from about 23 bar to about 24 bar, or from about 24 bar to about 25 bar), or from about 25 bar to about 30 bar (e.g., from about 25 bar to about 26 bar, from about 26 bar to about 27 bar, from about 27 bar to about 28 bar, from about 28 bar to about 29 bar, or from about 29 bar to about 30 bar). In certain embodiments, the pressure of the top of the absorber column is from about 20 bar to about 25 bar. In certain embodiments, the pressure of the top of the absorber column is from about 23 bar to about 24 bar. In certain embodiments, the pressure of the top of the absorber column is from about 23 bar to about 24 bar. In certain embodiments, the pressure of the top of the absorber column is about 20 bar, about 21 bar, about 22 bar, about 23 bar, about 24 bar, about 25 bar, about 26 bar, about 27 bar, about 28 bar, about 29 bar, or about 30 bar. In certain embodiments, the pressure of the top of the absorber column is about 24 bar. In certain embodiments, the pressure of the top of the absorber column is about 23.5 bar. The pressure of the bottom of the absorber column can be maintained from about 10 bar to about 40 bar. In certain embodiments, the pressure of the bottom of the absorber column is from about 20 bar to about 30 bar, e.g., from about 20 bar to about 25 bar (e.g., from about 20 bar to about 21 bar, from about 21 bar to about 22 bar, from about 22 bar to about 23 bar, from about 23 bar to about 24 bar, or from about 24 bar to about 25 bar), or from about 25 bar to about 30 bar (e.g., from about 25 bar to about 26 bar, from about 26 bar to about 27 bar, from about 27 bar to about 28 bar, from about 28 bar to about 29 bar, or from about 29 bar to about 30 bar). In certain embodiments, the pressure of the bottom of the absorber column is from about 20 bar to about 25 bar. In certain embodiments, the pressure of the bottom of the absorber column is from about 23 bar to about 24 bar. In certain embodiments, the pressure of the bottom of the absorber column is about 20 bar, about 21 bar, about 22 bar, about 23 bar, about 24 bar, about 25 bar, about 26 bar, about 27 bar, about 28 bar, about 29 bar, or about 30 bar. In certain embodiments, the pressure of the bottom of the absorber column is about 24 bar. In certain embodiments, the pressure of the bottom of the absorber column is about 23.7 bar. In certain embodiments, the pressure of the top of the absorber column is the same as the pressure of the bottom of the absorber column, e.g., a pressure in the range of from about 23 bar to about 24 bar. In certain embodiments, the pressure of the bottom of the absorber column is about 24 bar. In certain embodiments, the pressure of the top of the absorber column is substantially the same as the pressure of the bottom of the absorber column, e.g., a pressure in the range of from about 23 bar to about 24 bar. In one non-limiting example, the pressure of the top of the absorber column is about 23.5 bar, and the pressure of the bottom of the absorber column is about 23.7 bar.

The temperature of the top and the bottom of the absorber column can be different, substantially the same, or the same. In certain embodiments, the temperature of the top of the absorber column is different from the bottom of the absorber column. In certain embodiments, the temperature of the top of the absorber column is higher than the temperature of the bottom of the absorber column. The temperature of the top of the absorber column can be maintained from about 5° C. to about 20° C. In certain embodiments, the temperature of the top of the absorber column is from about 5° C. to about 10° C., e.g., from about 5° C. to about 6° C., from about 6° C. to about 7° C., from about 7° C. to about 8° C., from about 8° C. to about 9° C., or from about 9° C. to about 10° C. In certain embodiments, the temperature of the top of the absorber column is from about 7° C. to about 8° C. In certain embodiments, the temperature of the top of the absorber column is about 5° C., about 6° C., about 7° C., about 8° C., about 9° C., or 10° C. In certain embodiments, the temperature of the top of the absorber column is about 7° C. In certain embodiments, the temperature of the top of the absorber column is about 8° C. In certain embodiments, the temperature of the top of the absorber column is about 7.5° C. The temperature of the bottom of the absorber column can be maintained from about 50° C. to about 250° C. In certain embodiments, the temperature of the bottom of the absorber column is from about 100° C. to about 200° C., e.g., from about 100° C. to about 150° C. (e.g., from about 100° C. to about 110° C., from about 110° C. to about 120° C., from about 120° C. to about 130° C., from about 130° C. to about 140° C., or from about 140° C. to about 150° C.), or from about 150° C. to about 200° C. (e.g., from about 150° C. to about 160° C., from about 160° C. to about 170° C., from about 170° C. to about 180° C., from about 180° C. to about 190° C., or from about 190° C. to about 200° C.). In certain embodiments, the temperature of the bottom of the absorber column is from about 100° C. to about 150° C. In certain embodiments, the temperature of the bottom of the absorber column is about 100° C., about 110° C., about 120° C., about 130° C., about 140° C., about 150° C., about 160° C., about 170° C., about 180° C., about 190° C., or about 200° C. In certain embodiments, the temperature of the bottom of the absorber column is from about 120° C.

The method 100 can include feeding the first stream withdrawn from the absorber column to a stripper column 105. In the stripper column, benzene is separated from the $C_3$ hydrocarbons 106. The stripper column can be any conventional distillation column that separates components based on the boiling point of the components. The method 100 can include removing a second stream including the $C_3$ hydrocarbons from the stripper column 107. In certain embodiments, the second stream is removed from the bottom of the stripper column. The method 100 can further include removing a fourth stream including the benzene solvent from the stripper column 109. In certain embodiments, the fourth stream is removed from the top of the stripper column.

The pressure of the top and the bottom of the stripper column can be different, substantially the same, or the same. The pressure of the top of the stripper column can be maintained from about 10 bar to about 40 bar. In certain embodiments, the pressure of the top of the stripper column is from about 20 bar to about 30 bar, e.g., from about 20 bar to about 25 bar (e.g., from about 20 bar to about 21 bar, from about 21 bar to about 22 bar, from about 22 bar to about 23 bar, from about 23 bar to about 24 bar, or from about 24 bar to about 25 bar), or from about 25 bar to about 30 bar (e.g., from about 25 bar to about 26 bar, from about 26 bar to about 27 bar, from about 27 bar to about 28 bar, from about 28 bar to about 29 bar, or from about 29 bar to about 30 bar). In certain embodiments, the pressure of the top of the stripper column is from about 20 bar to about 25 bar. In certain embodiments, the pressure of the top of the stripper column is from about 22 bar to about 23 bar. In certain embodiments, the pressure of the top of the stripper column is about 20 bar, about 21 bar, about 22 bar, about 23 bar, about 24 bar, about 25 bar, about 26 bar, about 27 bar, about 28 bar, about 29 bar, or about 30 bar. In certain embodiments, the pressure of the top of the stripper column is about 22 bar. The pressure of the bottom of the stripper column can be maintained from about 10 bar to about 40 bar. In certain embodiments, the pressure of the bottom of the stripper column is from about 20 bar to about 30 bar, e.g., from about 20 bar to about 25 bar (e.g., from about 20 bar to about 21 bar, from about 21 bar to about 22 bar, from about 22 bar to about 23 bar, from about 23 bar to about 24 bar, or from about 24 bar to about 25 bar), or from about 25 bar to about 30 bar (e.g., from about 25 bar to about 26 bar, from about 26 bar to about 27 bar, from about 27 bar to about 28 bar, from about 28 bar to about 29 bar, or from about 29 bar to about 30 bar). In certain embodiments, the pressure of the bottom of the stripper column is from about 20 bar to about 25 bar. In certain embodiments, the pressure of the bottom of the stripper column is from about 22 bar to about 23 bar. In certain embodiments, the pressure of the bottom of the stripper column is about 22 bar. In certain embodiments, the pressure of the bottom of the stripper column is about 22.2 bar. In certain embodiments, the pressure of the top of the stripper column is the same as the pressure of the bottom of the stripper column, e.g., a pressure in the range of from about 22 bar to about 23 bar. In certain embodiments, the pressure of the top of the stripper column is substantially the same as the pressure of the bottom of the stripper column, e.g., a pressure in the range of from about 22 bar to about 23 bar. In one non-limiting example, the pressure of the top of the stripper column is about 22 bar, and the pressure of the bottom of the stripper column is about 22.2 bar.

The temperature of the top and the bottom of the stripper column can be different, substantially the same, or the same. In certain embodiments, the temperature of the top of the stripper column is different from the bottom of the stripper column. In certain embodiments, the temperature of the top of the stripper column is higher than the temperature of the bottom of the stripper column. The temperature of the top of the stripper column can be maintained from about 40° C. to about 70° C. In certain embodiments, the temperature of the top of the stripper column is from about 50° C. to about 60° C., e.g., from about 50° C. to about 55° C. (e.g., from about 50° C. to about 51° C., from about 51° C. to about 52° C., from about 52° C. to about 53° C., from about 53° C. to about 54° C., or from about 54° C. to about 55° C.), or from about 55° C. to about 60° C. (e.g., from about 55° C. to about 56° C., from about 56° C. to about 57° C., from about 57° C. to about 58° C., from about 58° C. to about 59° C., or from about 59° C. to about 60° C.). In certain embodiments, the temperature of the top of the stripper column is from about 55° C. to about 60° C. In certain embodiments, the temperature of the top of the stripper column is about 50° C., about 51° C., about 52° C., about 53° C., about 54° C., about 55° C., about 56° C., about 57° C., about 58° C., about 59° C., or about 60° C. In certain embodiments, the temperature of the top of the stripper column is about 57° C. The temperature of the bottom of the stripper column can be maintained from about 100° C. to about 400° C. In certain embodiments, the temperature of the bottom of the stripper column is from about 200° C. to about 300° C., e.g., from about 200° C. to about 250° C. (e.g., from about 200° C. to about 210° C., from about 210° C. to about 220° C., from about 220° C. to about 230° C., from about 230° C. to about 240° C., or from about 240° C. to about 250° C.), or from about 250° C. to about 300° C. (e.g., from about 250° C. to about 260° C., from about 260° C. to about 270° C., from about 270° C. to about 280° C., from about 280° C. to about 290° C., or from about 290° C. to about 300° C.). In certain embodiments, the temperature of the bottom of the stripper column is from about 220° C. to about 230° C. In certain embodiments, the temperature of the bottom of the stripper column is about 200° C., about 210° C., about 220° C., about 230° C., about 240° C., about 250° C., about 260° C., about 270° C., about 280° C., about 290° C., or about 300° C. In certain embodiments, the temperature of the bottom of the stripper column is from about 230° C. In certain embodiments, the temperature of the bottom of the stripper column is from about 228° C.

Benzene can be reused in the absorber column. In certain embodiments, the method 100 further includes feeding the fourth stream to the absorber column 110. The method can further include purging the fourth stream prior to feeding to the absorber column so that impurities do not buildup.

Benzene is neither a high volatile component nor low volatile component. Solvents with a low boiling point are usually included in the top stream of the stripper column if low temperature is used in the bottom of the stripper column. In order to not include a solvent with a high boiling point in the top stream of the stripper column, very high temperatures are required in a reboiler and very high pressure steam are required in the stripper column. Because of the unique boiling point of benzene, benzene is not present in the second stream including the $C_3$ hydrocarbons removed from the top of the stripper column due to its low volatility even if a low temperature is used in the bottom of the stripper column. Also because of the unique boiling point of benzene, a very high temperature at a reboiler is not required to separate benzene from the $C_3$ hydrocarbons in the stripper column so that benzene is not present in the second stream including the $C_3$ hydrocarbons removed from the top of the stripper column.

Figure 2:
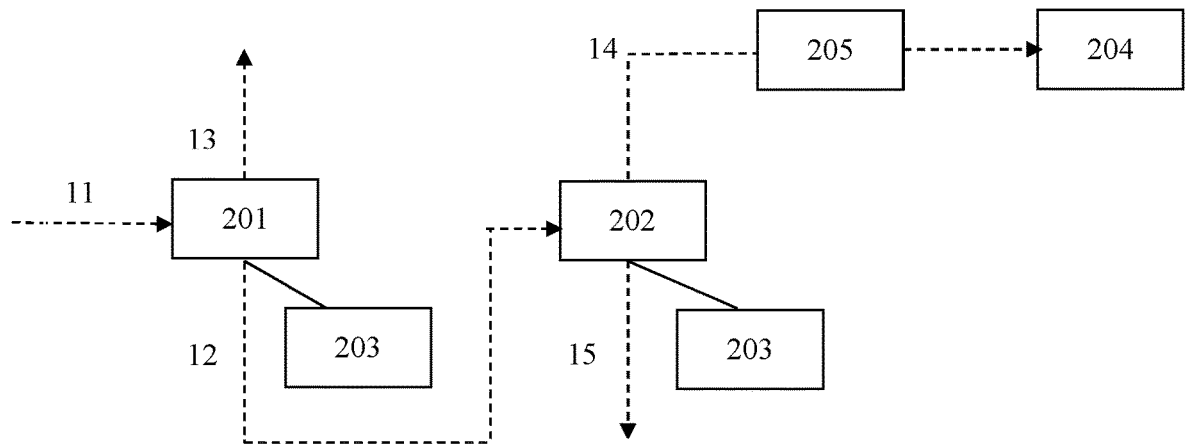
FIG. 2 is a schematic diagram depicting an exemplary system in accordance with one non-limiting embodiment of the disclosed subject matter.

The presently disclosed subject matter further provides a system for separating $C_3$ hydrocarbons from a gaseous mixture including lighter hydrocarbons ($C_1$ and $C_2$), $H_2$, CO, and/or $CO_2$, or combinations thereof, using a benzene solvent. For the purpose of illustration and not limitation, FIG. 2 is a schematic representation of an exemplary system according to the disclosed subject matter.

In certain embodiments, the system 200 can include an absorber column 201 for separating $C_3$ hydrocarbons from lighter hydrocarbons ($C_1$ and $C_2$), $H_2$, CO, and/or $CO_2$, or combinations thereof, through selective absorption of $C_3$ hydrocarbons by benzene and to promote the selective absorption of $C_3$ hydrocarbons from the gaseous mixture by the benzene solvent. The absorber column 201 is configured to receive the benzene solvent and the gaseous mixture. A gaseous mixture 11 including $C_3$ hydrocarbons, lighter hydrocarbons ($C_1$ and $C_2$), $H_2$, CO, and/or $CO_2$, or combinations thereof, can be fed to the absorber column 201. Benzene solvent 12 can be fed to the absorber column 201. In certain embodiments, the benzene solvent 12 is in countercurrent contact with the gaseous mixture 11. In certain embodiments, the benzene solvent 12 is fed to the top of the absorber column 201. In certain embodiments, the gaseous mixture 11 is fed to the side of the absorber column 201. A first stream 13 including benzene and absorbed $C_3$ hydrocarbons can be removed from the bottom of the absorber column 201. A third stream 14 including unabsorbed lighter hydrocarbons ($C_1$ and $C_2$), $H_2$, CO, and $CO_2$ can be removed from the top of the absorber column 201.

The system 200 further includes a stripper column 202 for separating benzene from the $C_3$ hydrocarbons. The stripper column 202 is configured to receive a first stream including the benzene solvent and absorbed $C_3$ hydrocarbons withdrawn from the absorber column, such that the benzene solvent is separated from $C_3$ hydrocarbons in the stripper column. The stripper column 202 is coupled to the absorber column 201. The first stream 12 withdrawn from the absorber column 201 can be fed to the stripper column 202. In certain embodiments, the first stream 12 is fed to the side of the stripper column 202. A second stream 15 including the $C_3$ hydrocarbons can be removed from the top of the stripper column 202. A fourth stream 16 including the benzene solvent can be removed from the bottom of the stripper column 202.

"Coupled" as used herein refers to the connection of a system component to another system component by any means known in the art. The type of coupling used to connect two or more system components can depend on the scale and operability of the system. For example, and not by way of limitation, coupling of two or more components of a system can include one or more joints, valves, fitting, coupling or sealing elements. Non-limiting examples of joints include threaded joints, soldered joints, welded joints, compression joints and mechanical joints. Non-limiting examples of fittings include coupling fittings, reducing coupling fittings, union fittings, tee fittings, cross fittings and flange fittings. Non-limiting examples of valves include gate valves, globe valves, ball valves, butterfly valves and check valves.

The system 200 can further include one or more reboilers coupled the absorber column 201 and/or the stripper column 202. In certain embodiments, the system includes a reboiler 203 coupled to the bottom of the absorber column 201. In certain embodiments, the system includes a reboiler 203 coupled to the bottom of the stripper column 202. The one or more reboilers can maintain the temperature of the bottom of the absorber column and/or the stripper column to a desired temperature, e.g., to maintain the temperature of the bottom of the absorber column to a temperature in the range of 100° C. to 150° C. (e.g., about 120° C.), and to maintain the temperature of the bottom of the stripper column to a temperature in the range of about 220° C. to about 230° C. (e.g., about 228° C.).

The system 200 can further include a $C_3$ stripper column 204 for separating propylene from other $C_3$ hydrocarbons, e.g., propane. The $C_3$ stripper column 204 is configured to receive a second stream including $C_3$ hydrocarbons withdrawn from the stripper column, such that propane is separated from propylene. The $C_3$ stripper column 204 can be coupled to top of the stripper column 202. The second stream 14 can be fed to the $C_3$ stripper column 204. Additionally, the system 200 can further include a condenser 205 coupled to the stripper column 202. In certain embodiments, the condenser 205 condense the second stream including $C_3$ hydrocarbons withdrawn from the stripper column from its gaseous to its liquid state, by cooling it. The condenser 205 can be positioned between the stripper column 202 and the $C_3$ stripper column 204 so that the second stream withdrawn from the top of the stripper column 202 can be condensed before entering the $C_3$ stripper column 204. The system 200 can further include a stripper cross exchanger coupled to the stripper column 202.

The presently disclosed techniques can include using benzene as a single/sole solvent. Benzene can have various advantages for separating $C_3$ hydrocarbons from a gaseous mixture including lighter hydrocarbons ($C_1$ and $C_2$), $H_2$, CO, and $CO_2$. For example, benzene can selectively absorb 99.9% of $C_3$ hydrocarbons. Benzene as a solvent requires much lower net energy compared to other similar solvents for the desired separation of $C_3$ hydrocarbons. As a single component solvent and chemically stable component, benzene has unique advantage over solvents with mixture of components (e.g., naptha). In addition, benzene is commercially available at a reasonable rate to be used as a solvent.

The presently disclosed subject matter can use a simple configuration of an Absorber column followed by a stripper column using conventional tray/packed towers as opposed to a complex coldbox configuration with multiple chilling levels, compressors, and a distillation column.

EXAMPLES

The following example is merely illustrative of the presently disclosed subject matter and should not be considered as a limitation in any way.

Example 1

Absorption of $C_3$ Hydrocarbons Using Benzene Solvent

Different solvents (Ranging from $C_5$ to $C_{10}$) were screened using process model built by commercially available Aspen Plus® software. PSRK equation of state thermodynamic model was chosen to represent the Vapor Liquid equilibrium behavior in the two towers. Net energy was required to achieve same separation for same feed flow rate. Results of Aspen Plus® simulation (see Table 1) showed that benzene required lower net energy for combined stripping and absorption operations.

TABLE 1

| Solvent | Solvent Flow rate ton/hour | Net Energy, MW |
|---|---|---|
| Iso Pentane ($C_5$) | 612 | 88.5 |
| Benzene ($C_6$) | 750 | 75.7 |
| Cyclo Hexane($C_6$) | 776 | 91.5 |
| Syn Naptha ($C_6$, $C_7$, $C_8$) | 715 | 100 |
| TX ($C_7$, $C_8$) | 763 | 81.5 |
| Decene ($C_{10}$) | 705 | 103 |

Aspen Plus® results for absorption of $C_3$ hydrocarbons using benzene as a solvent is given in Table 2 below. The results were based on 650KTPA production of propylene, steam to hydrocarbon ratio of 2.5, a reactor temperature of 550° C., reactor effluent following table shows results of simulation.

TABLE 2

| Stream Name | 1 | 2 | 4 | 7 | 8 |
|---|---|---|---|---|---|
| Temperature C. | 50 | 8 | 57.3 | 4.7 | 5 |
| Pressure bar | 24.868 | 23.5 | 22 | 24 | 24 |
| Vapor Frac | 1 | 1 | 0 | 0 | 0 |
| Mass Flow kg/hr | 222047.6 | 8343.154 | 213822 | 749807.5 | 193 |
| Mass Frac | | | | | |
| $H_2$ | 0.017 | 0.463 | trace | trace | 0 |
| CO | 0.001 | 0.033 | trace | trace | 0 |
| $CO_2$ | 0.006 | 0.156 | 1 PPM | trace | 0 |
| Methane | 0.001 | 0.028 | trace | trace | 0 |
| Ethylene | 0.002 | 0.05 | 5 PPM | trace | 0 |
| Ethane | 0.007 | 0.176 | 180 PPM | trace | 0 |
| Propylene | 0.346 | 0.02 | 0.358 | 150 PPM | 0 |
| Propane | 0.618 | 0.019 | 0.64 | 301 PPM | 0 |
| 1 butane | 50 PPM | 1 PPB | 47 PPM | 1 PPM | 0 |
| 1 butene | 107 PPB | trace | 92 PPB | 6 PPB | 0 |
| Ma | 0.001 | 297 PPB | 0.001 | 9 PPM | 0 |
| Pd | 0.0005 | 297 PPB | 0.0005 | 9 PPM | 0 |
| Benzene | 13 PPM | 0.056 | 30 PPM | 1 | 1 |

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for separating $C_3$ hydrocarbons from a gaseous mixture, the method comprising:
   (a) feeding the gaseous mixture comprising $C_1$ hydrocarbons, $C_2$ hydrocarbons, and $C_3$ hydrocarbons to an absorber column;
   (b) feeding benzene solvent to the absorber column, wherein benzene solvent selectively absorbs $C_3$ hydrocarbons;
   (c) removing a first stream comprising benzene solvent and absorbed $C_3$ hydrocarbons from the absorber column;
   (d) feeding the first stream to a stripper column where benzene solvent is separated from $C_3$ hydrocarbons; and
   (e) removing a second stream comprising $C_3$ hydrocarbons from the stripper column;
   wherein the benzene solvent is in concurrent contact with the gaseous mixture; and
   wherein the gaseous mixture further comprises at least one member selected from the group consisting of carbon monoxide, carbon dioxide and water.

2. The method of claim 1, wherein the gaseous mixture further comprises carbon monoxide.

3. The method of claim 1, wherein the wherein the gaseous mixture further comprises carbon dioxide.

4. The method of claim 1, wherein the gaseous mixture further comprises water.

5. The method of claim 1, wherein the weight ratio of the benzene solvent fed to the absorber column to the gaseous mixture fed to the absorber column is 4:1 (ton/ton).

6. The method of claim 1, further comprising removing a third stream comprising $C_1$ and $C_2$ hydrocarbons from the absorber column.

7. The method of claim 6, further comprising removing a fourth stream comprising benzene solvent from the stripper column.

8. The method claim 7, further comprising feeding the fourth stream to the absorber column.

9. The method of claim 1, further comprising feeding the second stream to a $C_3$ stripper column to separate propane from propylene.

10. The method of claim 1, wherein the weight ratio of the benzene solvent fed to the absorber column to the gaseous mixture fed to the absorber column is 3:1 (ton/ton).

11. The method of claim 1, wherein the weight ratio of the benzene solvent fed to the absorber column to the gaseous mixture fed to the absorber column is from about 3:1 to about 4:1 (ton/ton).

12. The method of claim 1, wherein the pressure of the absorber column is maintained at a pressure of from about 23 bar to about 24 bar.

13. The method of claim 1, wherein the pressure of the stripper column is maintained at a pressure of from about 22 bar to about 23 bar.

14. The method of claim 1, wherein the temperature of the top of the absorber column is maintained at a temperature of from about 7° C. to about 8° C.

15. The method of claim 1, wherein the temperature of the bottom of the absorber column is maintained at a temperature of from about 100° C. to about 150° C.

16. The method of claim 1, wherein the temperature of the top of the stripper column is maintained at a temperature of from about 50° C. to about 60° C.

17. The method of claim 1, wherein the temperature of the bottom of the stripper column is maintained at a temperature of from about 220° C. to about 230° C.

18. The method of claim 1, wherein the weight ratio of the benzene solvent fed to the absorber column to the gaseous mixture fed to the absorber column is 3.6:1 (ton/ton).

19. A method for separating $C_3$ hydrocarbons from a gaseous mixture, the method consisting of the steps of:
   (a) feeding the gaseous mixture consisting of methane, ethane, ethylene, carbon monoxide, carbon dioxide, and $C_3$ hydrocarbons to an absorber column;
   (b) feeding benzene solvent to the absorber column, wherein benzene solvent selectively absorbs $C_3$ hydrocarbons;
   (c) removing a first stream comprising benzene solvent and absorbed $C_3$ hydrocarbons from the absorber column;
   (d) feeding the first stream to a stripper column where benzene solvent is separated from $C_3$ hydrocarbons; and
   (e) removing a second stream comprising $C_3$ hydrocarbons from the stripper column;
   wherein the benzene solvent is in concurrent contact with the gaseous mixture;
   wherein the temperature of the top of the stripper column is maintained at a temperature of 60° C.;
   wherein the temperature of the bottom of the stripper column is maintained at a temperature of 230° C.;
   wherein the temperature of the top of the absorber column is maintained at a temperature of 8° C.;
   wherein the pressure of the absorber column is maintained at a pressure of 24 bar; and
   wherein the pressure of the stripper column is maintained at a pressure of 23 bar.

20. A method for separating $C_3$ hydrocarbons from a gaseous mixture, the method consisting of the steps of:
   (a) feeding the gaseous mixture consisting of methane, ethane, ethylene, carbon monoxide, carbon dioxide, and $C_3$ hydrocarbons to an absorber column;
   (b) feeding benzene solvent to the absorber column, wherein benzene solvent selectively absorbs $C_3$ hydrocarbons;
   (c) removing a first stream comprising benzene solvent and absorbed $C_3$ hydrocarbons from the absorber column;
   (d) feeding the first stream to a stripper column where benzene solvent is separated from $C_3$ hydrocarbons; and
   (e) removing a second stream comprising $C_3$ hydrocarbons from the stripper column;
   wherein the benzene solvent is in concurrent contact with the gaseous mixture;
   wherein the temperature of the top of the stripper column is maintained at a temperature of 50° C.
   wherein the temperature of the bottom of the stripper column is maintained at a temperature of 220° C.;
   wherein the temperature of the top of the absorber column is maintained at a temperature of 7° C.;
   wherein the pressure of the absorber column is maintained at a pressure of 23 bar; and
   wherein the pressure of the stripper column is maintained at a pressure of 22 bar.

* * * * *